(12) United States Patent  (10) Patent No.: US 9,101,319 B2
Kojima  (45) Date of Patent: Aug. 11, 2015

(54) MOBILE X-RAY DEVICE AND METHOD FOR CONTROLLING MOBILE X-RAY DEVICE

(75) Inventor: Akira Kojima, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 282 days.

(21) Appl. No.: 13/641,942

(22) PCT Filed: Apr. 20, 2011

(86) PCT No.: PCT/JP2011/059674
§ 371 (c)(1),
(2), (4) Date: Oct. 18, 2012

(87) PCT Pub. No.: WO2011/136094
PCT Pub. Date: Nov. 3, 2011

(65) Prior Publication Data
US 2013/0039473 A1   Feb. 14, 2013

(30) Foreign Application Priority Data
Apr. 26, 2010 (JP) .................... 2010-100559

(51) Int. Cl.
*H05G 1/02* (2006.01)
*A61B 6/00* (2006.01)

(52) U.S. Cl.
CPC ............ *A61B 6/4405* (2013.01); *A61B 6/547* (2013.01); *A61B 6/56* (2013.01)

(58) Field of Classification Search
CPC ............... A61B 6/4405; A61B 2560/0214; H05G 1/58
USPC .......................................... 378/198
See application file for complete search history.

(56) References Cited

U.S. PATENT DOCUMENTS

| | | | | |
|---|---|---|---|---|
| 7,016,467 B2 * | 3/2006 | Brooks | .......................... | 378/102 |
| 7,309,159 B2 * | 12/2007 | Watanabe | ..................... | 378/198 |
| 7,438,470 B2 * | 10/2008 | Koren | ............................ | 378/198 |
| 8,523,433 B2 * | 9/2013 | Butzine et al. | ................ | 378/198 |
| 2006/0120512 A1 * | 6/2006 | Watanabe | ..................... | 378/198 |
| 2008/0025469 A1 * | 1/2008 | Watanabe | ..................... | 378/198 |
| 2011/0123001 A1 * | 5/2011 | Kopcienski et al. | ........... | 378/198 |
| 2012/0008748 A1 * | 1/2012 | Fuse et al. | ...................... | 378/98 |
| 2012/0163543 A1 * | 6/2012 | Fuse et al. | ...................... | 378/96 |

FOREIGN PATENT DOCUMENTS

| | | |
|---|---|---|
| JP | 2-024655 | 7/1990 |
| JP | 5-093404 | 4/1993 |
| JP | 5-093405 | 4/1993 |
| JP | 1999-099145 | 4/1999 |

(Continued)

OTHER PUBLICATIONS

International Search Report from International Application No. PCT/JP2011/059674 Mailed Jun. 7, 2011.

*Primary Examiner* — Michael Maskell
(74) *Attorney, Agent, or Firm* — Brundidge & Stanger, P.C.

(57) ABSTRACT

Provided is a mobile X-ray device with which the power consumption of the battery of the mobile X-ray device can be reduced efficiently by determining the state of movement of the mobile X-ray device from the states of the components thereof and controlling the supply of electric power to the components in non-movement-related sections, which are sections irrelevant to the movement of the mobile X-ray device.

9 Claims, 9 Drawing Sheets

(56) References Cited

FOREIGN PATENT DOCUMENTS

| JP | 2006-158508 | 6/2006 |
| JP | 2006-239070 | 9/2006 |
| JP | 2008-073121 | 3/2008 |
| JP | 2009-201561 | 9/2009 |

\* cited by examiner

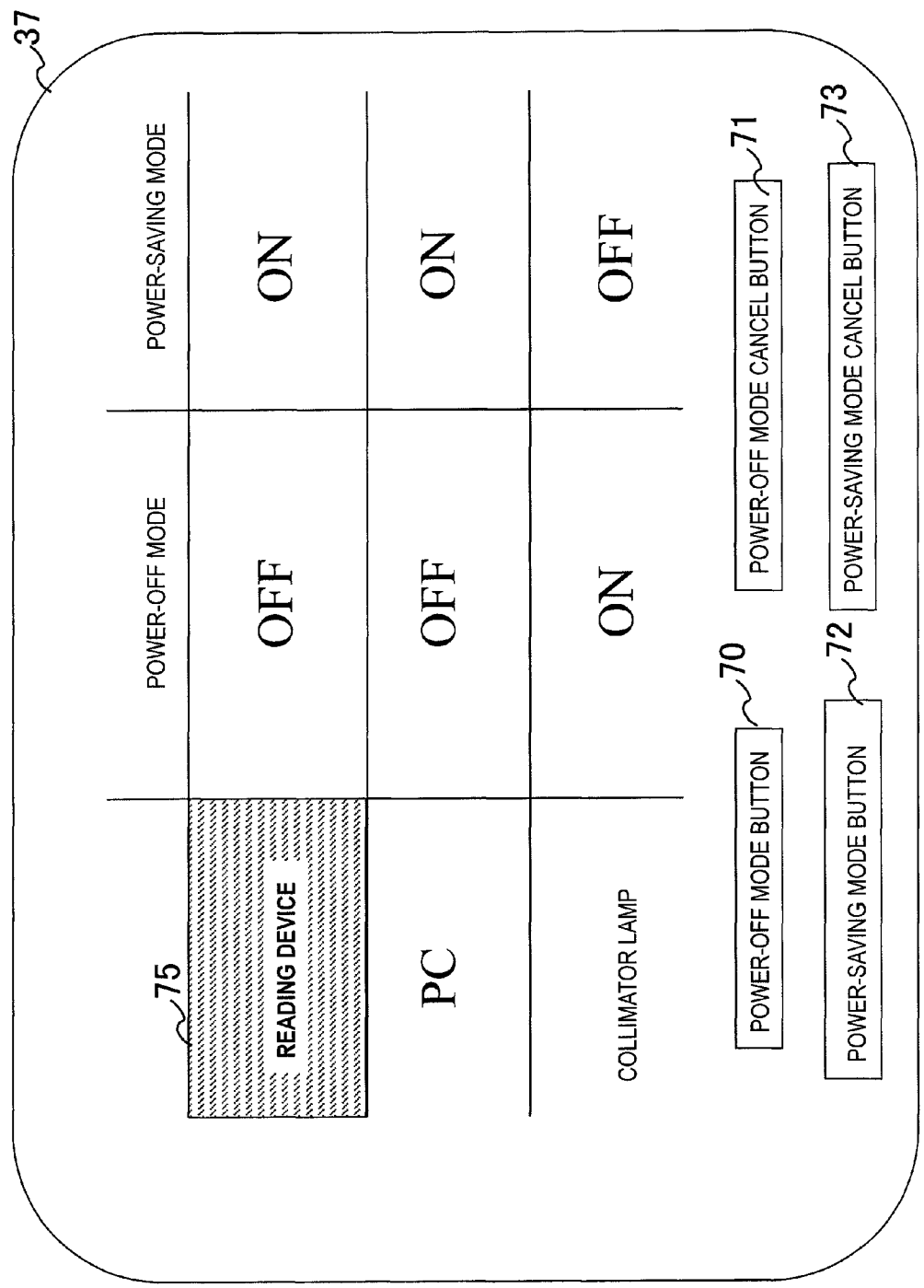

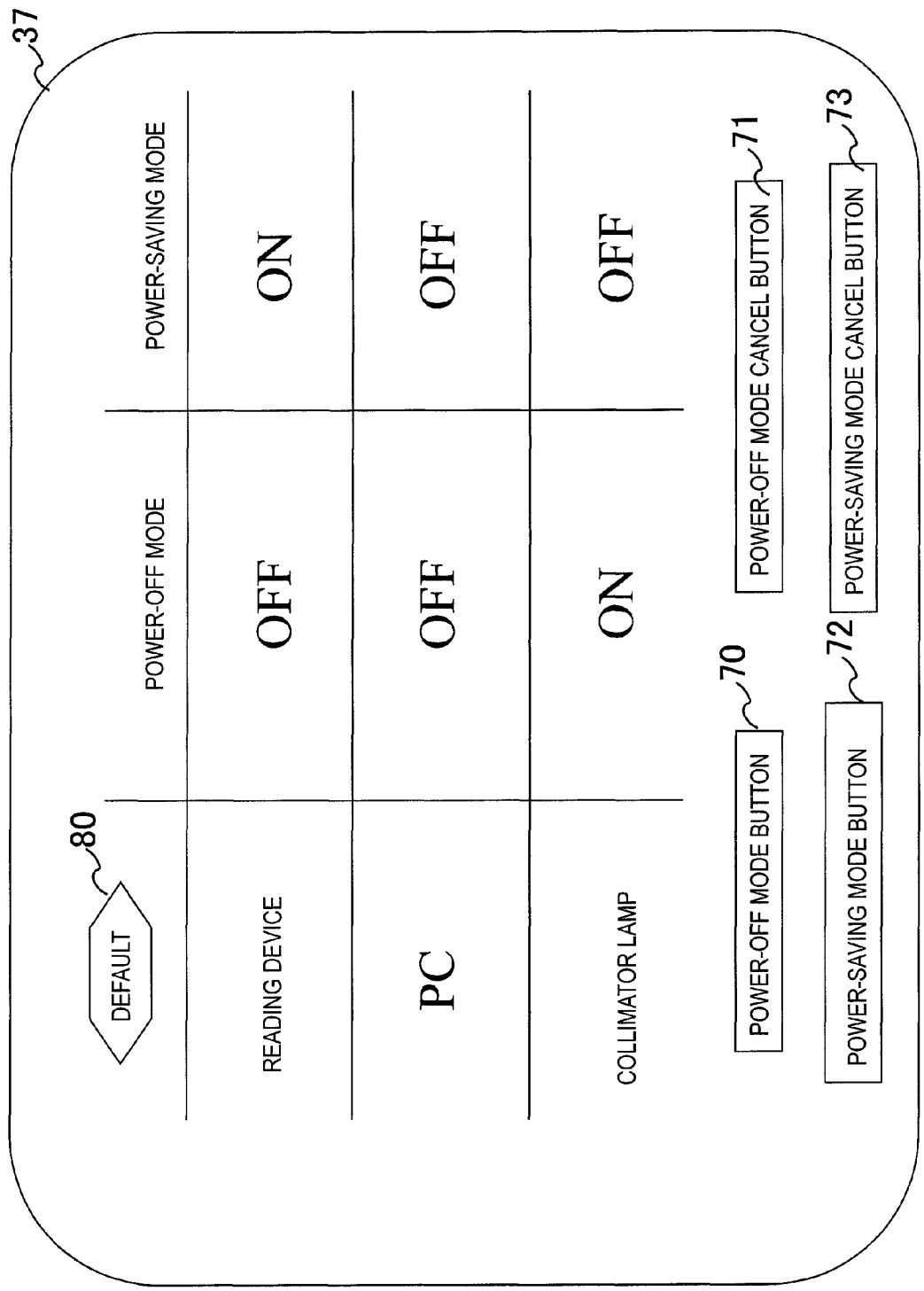

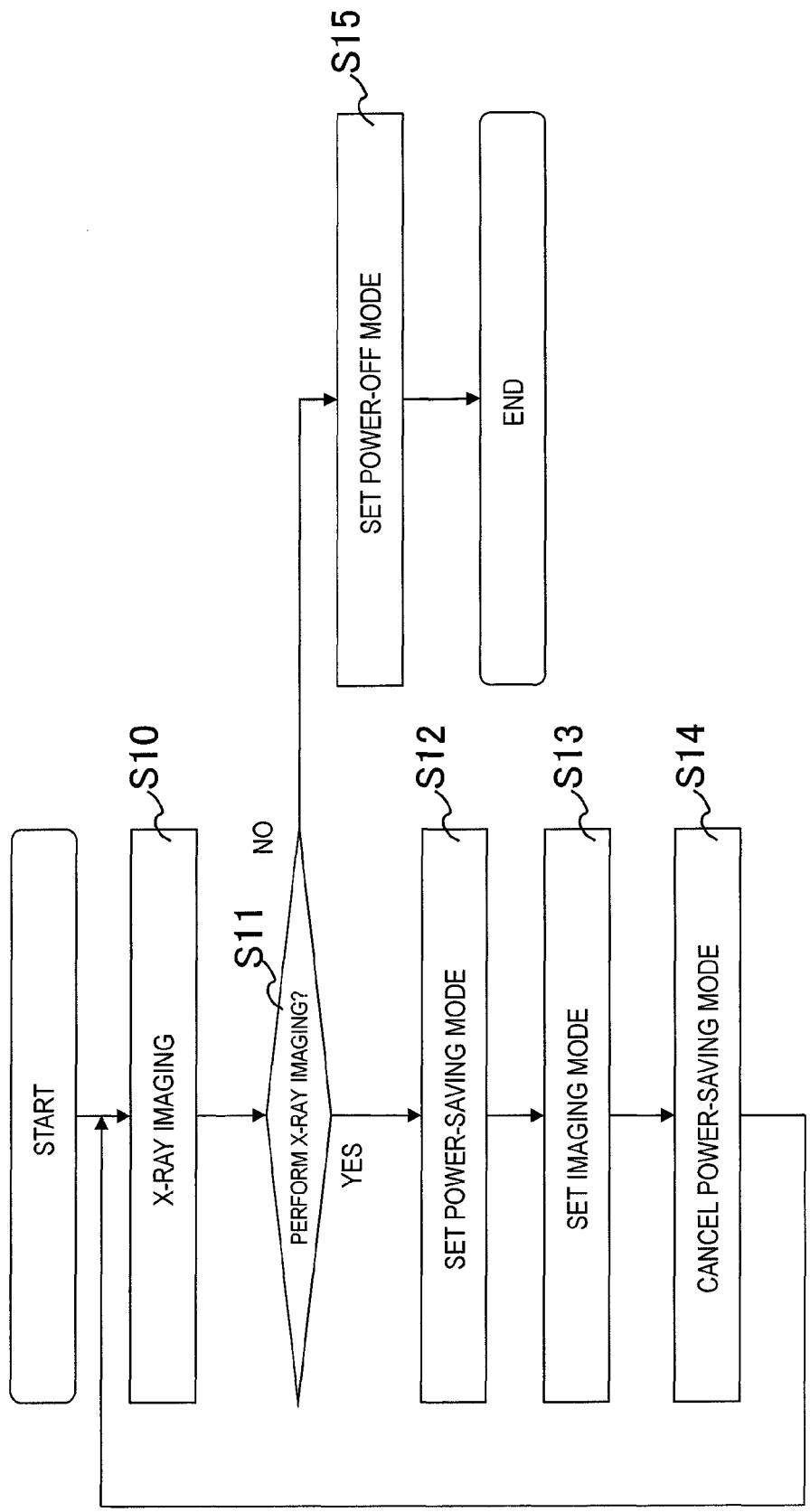

MOBILE X-RAY DEVICE AND METHOD FOR CONTROLLING MOBILE X-RAY DEVICE

FIELD OF THE INVENTION

The present invention relates to a mobile X-ray device and the method for controlling the mobile X-ray device capable of moving around in a hospital to perform X-ray imaging.

DESCRIPTION OF RELATED ART

A mobile X-ray device is a type of medical X-ray apparatus capable of moving around in a hospitals to perform X-ray imaging, which is mainly used for performing X-ray imaging for the patients who are incapable of moving within their rooms or within an operating room, or the patients in urgent situations.

A prior technique is disclosed, in the case that a mobile X-ray device is placed outside of a patient's room, which detects the positional information of a mobile X-ray device via a remote transmitter/receiver, sets a reading device that reads out nuclear image information from a cassette to which an X-ray is irradiated in the power-saving mode, and turns off the unnecessary power to the display, etc. (for example, Patent Document 1)

PRIOR ART

Patent Document

Patent Document 1: JP-A-2008-73121

However, the condition that a remote transmitter/receiver is not provided in a patient's room is not considered in the mobile X-ray device disclosed in Patent Document 1. Therefore, the positional information of the mobile X-ray device cannot be detected in the patient's room where a remote transmitter/receiver is not provided, and the reading device of the mobile X-ray device cannot be set on power-saving mode or the electric power to the unnecessary devices cannot be turned off.

Given this factor, the objective of the present invention is to detect the movement condition of the mobile X-ray device from the state of the components in the mobile X-ray device and control the power supply to the components that are irrelevant to the movement of the mobile X-ray device, so as to effectively minimize the power consumption in the battery of the mobile X-ray device.

BRIEF SUMMARY OF THE INVENTION

In order to achieve the above-described objective, the mobile X-ray device of the present invention comprises:
a main body;
a carriage on which the main body is mounted;
an X-ray generation unit provided with an X-ray tube for generating an X-ray;
an X-ray collimator configured to adjust the irradiating field of the X-ray;
an arm configured to support the X-ray generation unit;
a columnar support which is disposed on the carriage for supporting the arm;
a battery for supplying electric power to the respective components;
a determination unit configured to determine the movement condition of the mobile X-ray device; and
a power setting unit configured to set the electric power to be supplied from the battery to the components that are irrelevant to the movement of the mobile X-ray on the basis of the movement condition which is determined by the determination unit. Accordingly, the movement condition of the mobile X-ray device can be detected from the condition of the components in the mobile X-ray device so that the power supply to the components that are irrelevant to the movement of the mobile X-ray device can be controlled.

Also, when the determination unit determines that the mobile X-ray device is in a moving mode, the power setting unit sets the power-off mode to turn off the electric power to be supplied from the battery to the components that are irrelevant to the movement of the mobile X-ray device. Also, when the determination unit determines that the mobile X-ray device is in a moving mode, the power supply unit sets the power-saving mode to minimize the electric power to be supplied from the battery to the components that are irrelevant to the movement of the mobile X-ray device. Also, when the determination unit determines that the mobile X-ray device is in a moving mode, the power supply unit supplies the electric power from the battery to the components that are relevant to the movement of the mobile X-ray device. Also, when the determination unit determines that the mobile X-ray device is in an imaging mode, the power supply unit turns off the electric power to be supplied from the battery to the components that are relevant to the movement of the mobile X-ray device.

Further, the present invention comprises an operation unit configured to select the power-off mode or the power-saving mode with respect to the electric power to be supplied to the components that are irrelevant to the movement of the mobile X-ray device.

Effect of the Invention

The present invention is capable of detecting the movement condition of the mobile X-ray device from the condition of the components in the mobile X-ray device and controlling the power supply to the components that are irrelevant to the movement of the mobile X-ray device. Accordingly, the power consumption of the battery in mobile X-ray device can be effectively minimized.

BRIEF DESCRIPTION OF THE DRAWINGS

FIG. 7 is a view showing a third embodiment of the mobile X-ray device related to the present invention.

FIG. 8 is a view showing a fourth embodiment of the mobile X-ray device related to the present invention.

FIG. 9 is a view showing a fifth embodiment of the mobile X-ray device related to the present invention.

DETAILED DESCRIPTION OF THE INVENTION

Figure 1:
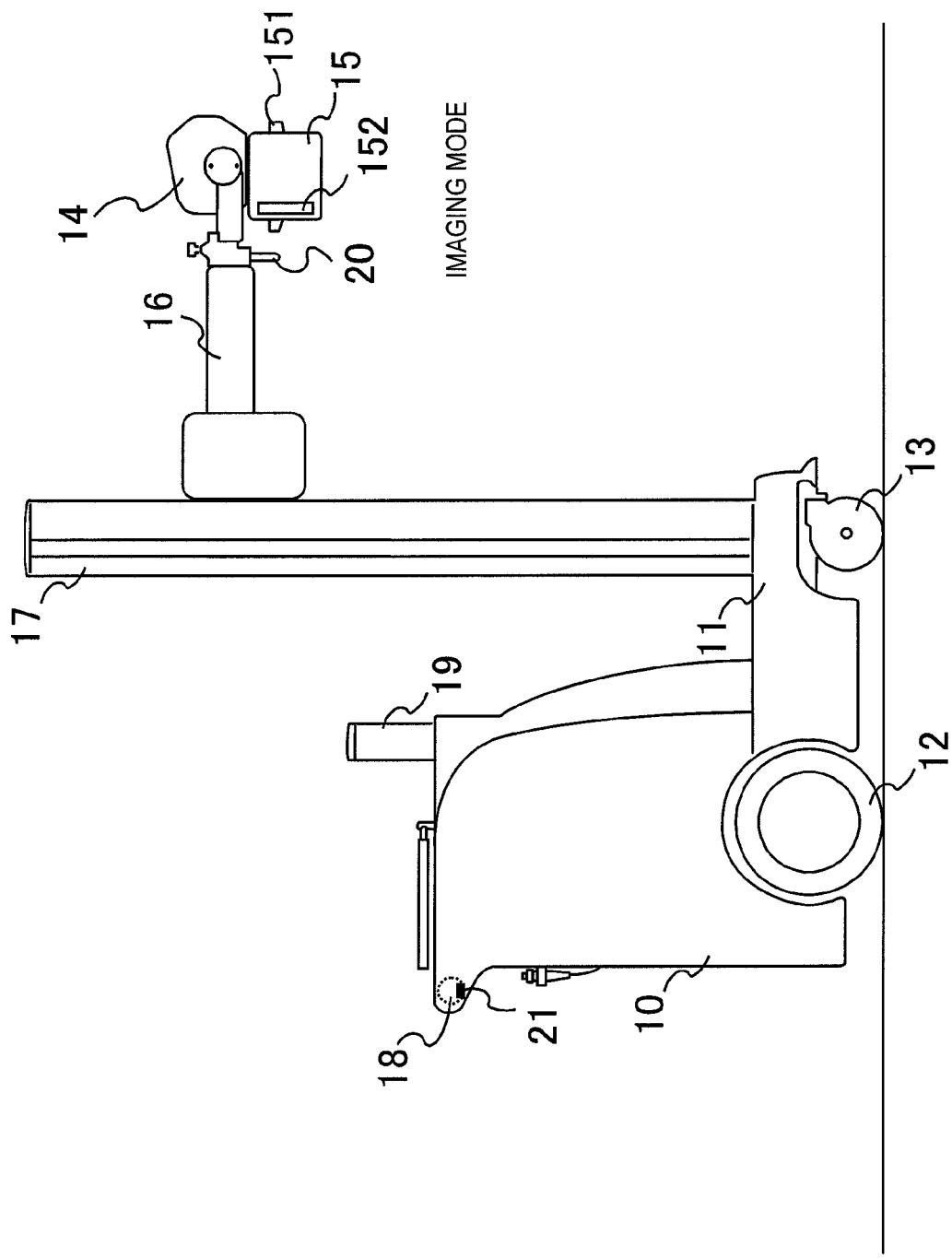
FIG. 1 is an overview showing an imaging mode of the mobile X-ray device related to the present invention.

The present invention will be described below referring to the drawings.

Embodiment 1

Figure 2:
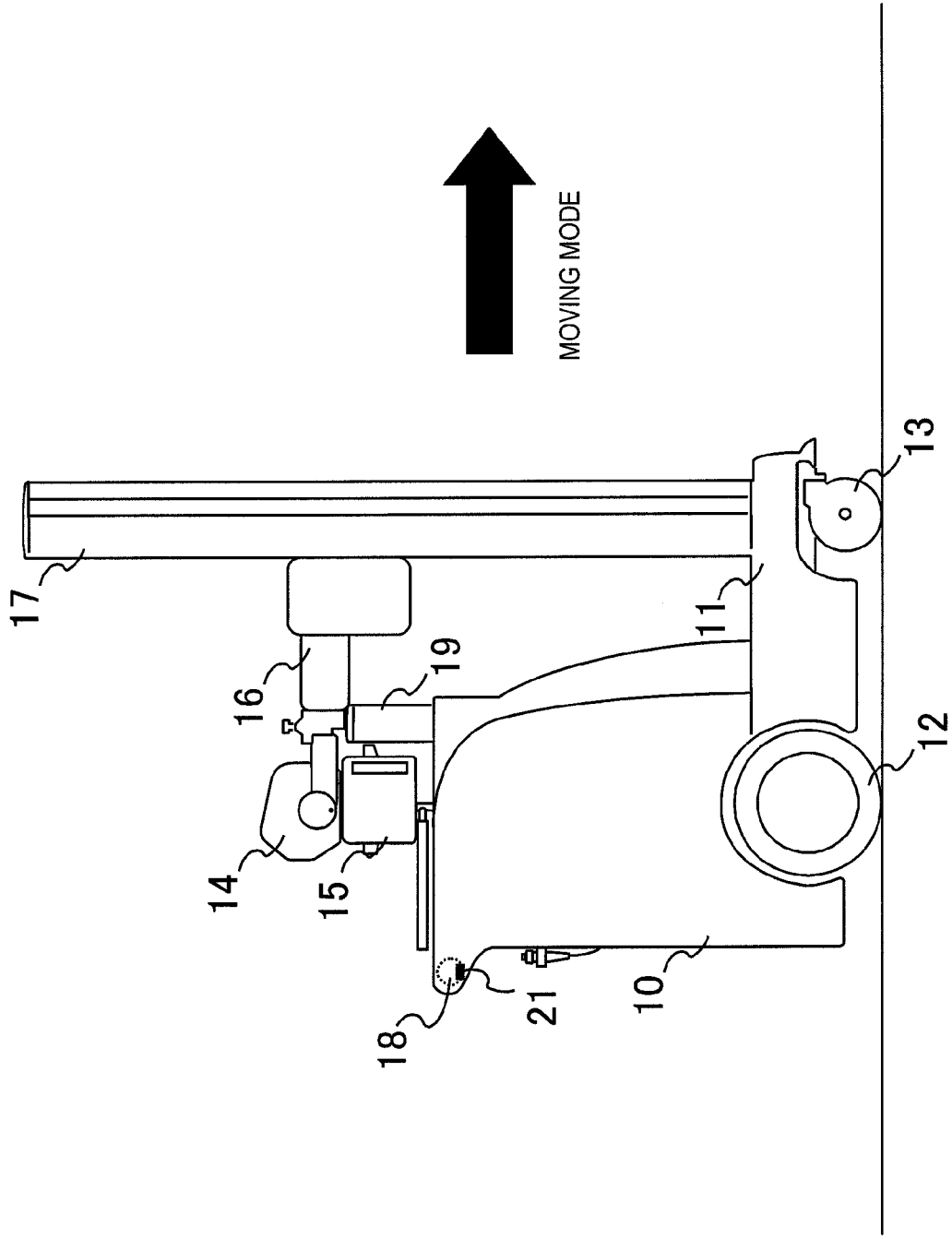
FIG. 2 is an overview showing a moving mode of the mobile X-ray device related to the present invention.

FIGS. 1 and 2 are overviews of a mobile X-ray device related to the present invention. FIG. 1 shows the state of the mobile X-ray device in an imaging mode for executing X-ray imaging, and FIG. 2 shows the state of the mobile X-ray device in a moving mode for transferring the mobile X-ray device.

The mobile X-ray device comprises:
a main body 10;
a carriage 11 on which the main body 10 is disposed, and provided with wheels 12 and 13 for transferring the main body 10, etc.;
an X-ray generation unit, provided with an X-ray tube for generating an X-ray, which is configured to generate an X-ray;
an X-ray collimator 15 configured to adjust the irradiation field of an X-ray;
an arm 16 configured to support the X-ray generation unit 14 and the X-ray collimator 15;
a columnar support 17 which is disposed on the carriage 11 for supporting the arm 16;
an operation handle 18 for an operator to operate the movement of the mobile X-ray device; and
an arm supporting unit 19 configured to hold and fix the arm 16 at the time that mobile X-ray device is transferred.

The X-ray generation unit 14 is provided with the X-ray tube which generates an X-ray and a high-voltage generation unit. The X-ray generation unit 14 generates an X-ray in accordance with the X-ray imaging condition which is set in advance.

The X-ray generation unit 14 and the X-ray collimator 15 are disposed on one end of the arm 16, and the other end of the arm 16 is supported slidably in the vertical and horizontal directions by the columnar support 17 which is disposed on the carriage 11. By extending the arm 16, the X-ray generation unit 14 and the X-ray collimator 15 can be protruded toward the moving direction of the main body. In this manner, the X-ray generation unit 14 and the X-ray collimator 15 can be placed over a bed.

The X-ray collimator 15 is provided with two pairs of mobile restricting blades for adjusting the irradiation range of an X-ray and an illumination lamp for illuminating the irradiation range of the X-ray. Also, in the periphery of the X-ray collimator 15, an operation grip 151 for controlling the mobile restricting blades and an illumination switch, etc. for lighting the illumination lamp are provided. By rotating the operation grip 151, two pairs of the mobile restricting blades can be opened and closed.

On both sides of the X-ray collimator 15, a concavo-convex shaped knobs 152 is disposed. On the inner side of the knob 152, a cancel switch for releasing the brake, put on the parts such as arm 16 and columnar 17, is respectively provided for moving the X-ray generation unit 14. When the operator grabs the knobs 152, the cancel switch is pushed by the fingers or palms of the operator to release the brake put on the arm 16 and the columnar support 17, etc. so that the X-ray generation unit 14 and the X-ray collimator 15 can be moved to arbitrary positions.

Also, when the operator releases his/her hands from the knobs 152, a brake can be put on the arm 16 and the columnar support 17 so that the X-ray generation unit 14 and the X-ray mobile can be fixed at a predetermined allocated position. In other words, the X-ray generation unit 14 and the X-ray collimator 15 are fixed at the position where the operator released his/her hands from the knobs 152.

Also, a rod-like guide pin 20 is disposed on the bottom surface of the arm 16. The guide pin 20 has a through-hole at its distal end. Meanwhile, a tubular arm holding unit 19 is disposed on the top surface of the carriage 11. The arm holding unit 19, though not shown in the diagram, is provided with a guide hole through which the guide pin 20 inserted and a fixation mechanism for fixing the guide pin 20. The fixation mechanism for fixing the guide pin 20 is configured, for example, by a rod portion to be inserted through the through-hole at the distal end of the guide pin 20.

After completing an X-ray imaging in the condition that the mobile X-ray device is in the imaging mode, the mobile X-ray device is transferred to another patient's room. At this time, the state of the mobile X-ray device is changed from the imaging mode shown in FIG. 1 (the arm 16 is on the right side with respect to the columnar support 17 (the side facing the main body 10)) to the moving mode shown in FIG. 2 (the arm 16 is on the left side with respect to the columnar support 17 (on the side of the main body 10)).

In concrete terms, in the imaging mode of the mobile X-ray device shown in FIG. 1, the columnar support 17 is rotated with respect to the carriage 11 centering around its vertical direction to move the arm 16 to the left side (the side of the main body 10) with respect to the columnar support 17. After the columnar support 17 is rotated, the arm 16 is disposed at the upper part of the carriage 11.

In the state that the arm 16 is placed at the upper part of the carriage 11, the arm 16 is contracted as well as slid toward the lower direction, and the rod-like guide pin 20 which is placed at the bottom surface of the arm 16 is inserted through the guide hole of the arm holding unit 19. In the state that the guide pin 20 is inserted into the guide hole of the arm holding unit 19, a rod portion (fixation mechanism) is inserted into the through-hole at the end of the guide pin 20 to fix the guide pin 20.

In this manner, when the arm-holding unit 19 holds and fixes the rod-like guide pin 20 which is disposed at the bottom surface of the arm 16, the arm 16 is integrated with the main body 10. Since such configuration allows compact storage of the arm 16, the operator can stably transfer the mobile X-ray device.

While a rod portion is used in the above-description to be inserted into a through-hole at the end of the guide pin 20 as a fixation mechanism of the arm holding unit 19, the guide pin 20 can also be fixed using a magnet, etc.

Here, the internal structure of the main body 10 in the mobile X-ray device related to the present invention will be described referring to FIG. 3. The main body of the mobile X-ray device is provided with an arm-holding detection unit 30 configured to detect the holding condition of the arm-holding unit 19, a power control unit 31 configured to control the power supply to the respective components, a wheel driving unit 32 configured to drive wheels 12, a wheel locking unit 33 configured to lock the wheels by putting the brake on the wheels 12, a reading device 34 configured to read the image data in the imaging plate to which an X-ray is irradiated, a PC (image storage/processing unit) 35 configured to store or execute image processing the image data read in from the reading device 34, a battery 38 in which electric power is charged via a device outside of the main body 10 such as a plug outlet to supply the electric power to the respective components, and an operation unit 37 configured to set the power condition, etc. of the respective components. Also, the X-ray collimator 15 incorporates an collimator lamp 36 configured to illuminate the irradiation range of an X-ray. Movement-related sections 40 that are relevant to the movement of the mobile X-ray device include, for example a movement switch 21, the power control unit 31, the wheel driving unit 32 and the wheel locking unit 33.

The movement switch 21 for driving the wheels 12 is disposed on the peripheral edge of the operation handle 18. When an operator grabs the operation handle 18, the moving switch 21 is pushed. In order to move the mobile X-ray device, in the moving mode shown in FIG. 2, the operator grabs the operation handle 18 and pushes the movement switch 21. When the movement switch 21 is pushed, the brake which is put on the wheels 12 by the wheel locking unit 33 is released. Then the wheel driving unit 32 detects the pressing information of the operation handle 18 grabbed by the operator and rotates the wheels 12 on the basis of the detected pressing information. The operator can move the mobile X-ray device by pushing the operation handle 18 to the arrow direction shown in FIG. 2 while grabbing it for moving the carriage 11. The movement of the mobile X-ray device becomes synonymous with the movement of the carriage 11. In order to stop the mobile X-ray device, the operator releases his/her hand from the operation handle 18 to release the mobile switch 21. When the movement switch 21 is released, driving of the wheels 12 by the wheel driving unit 32 is ceased, and a brake is put on the wheels 12 by the wheel locking unit 33. Wheels 13 are the auxiliary wheels.

Figure 3:
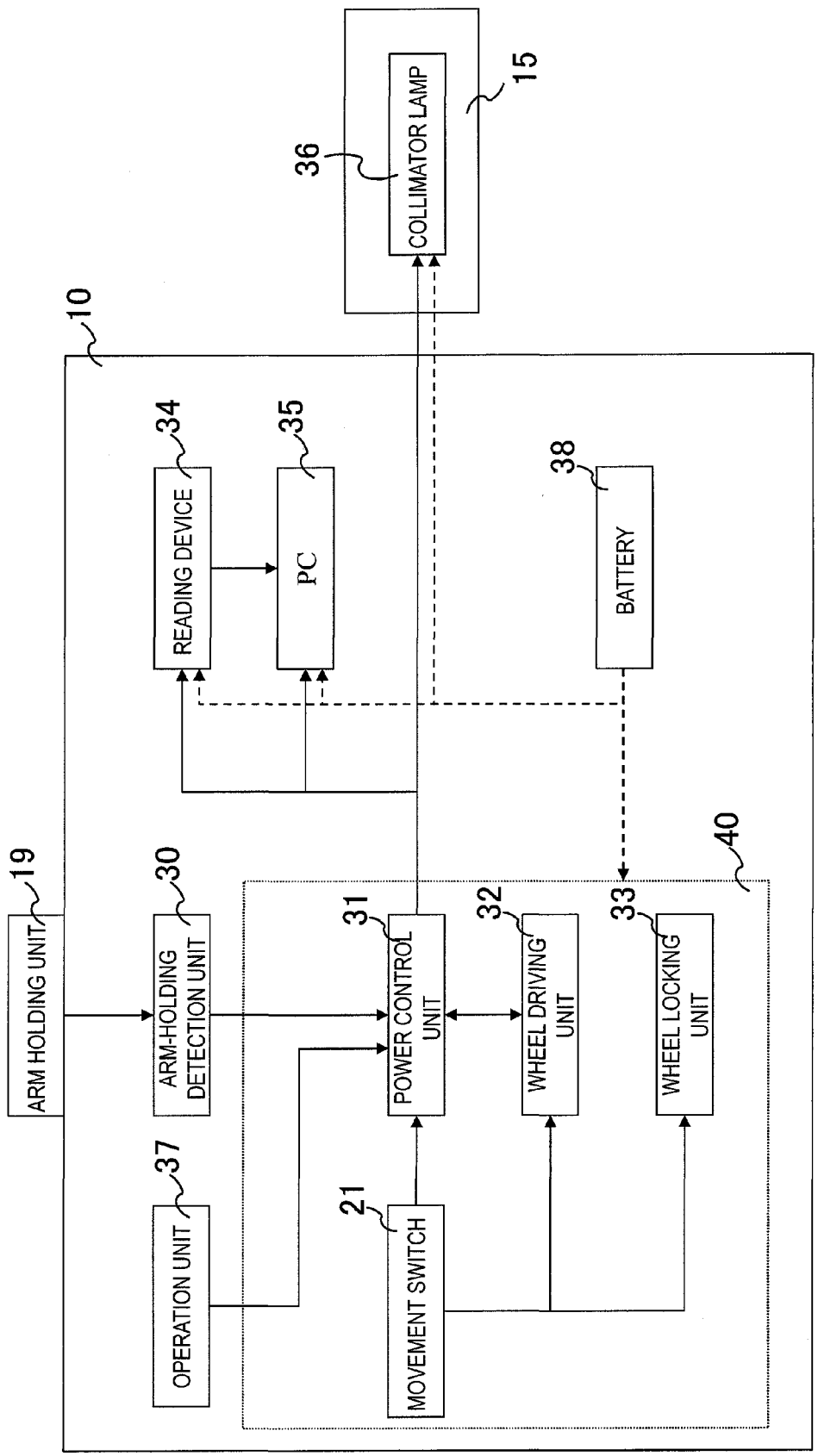
FIG. 3 is a view of an internal structure in a main body 10 of the mobile X-ray device related to the present invention.

The dotted lines shown in FIG. 3 indicate the supply route of the electric power from the battery 38 to the respective components. The battery 38 can provide power at least to the respective components of the movement-related sections 40, the reading device 34, the PC 35 and the collimator lamp 36.

The arm-holding detection unit 30 detects whether or not the rod-like guide pin 20 disposed at the bottom surface of the arm 16 is held by the arm-holding unit 19, so as to detect the holding condition of the arm 16. In concrete terms, a light sensor (not shown) configured to detect the guide pin 20 which is inserted into the arm-holding unit 19 is disposed in the guide hole of the arm-holding unit 19.

The light sensor is formed by an illumination unit configured to irradiate a light and an illumination detecting unit which is disposed facing the illumination unit in the guide hole configured to detect the light irradiated from the irradiation unit. When the arm 16 (guide pin 20) is held by the arm-holding unit 19, the light irradiated from the illumination unit is blocked by the guide pin 20 which is inserted into the guide hole of the arm-holding unit 19, thus the light which is irradiated from the illumination unit is not detected by the illumination detecting unit. At this time, the arm-holding detection unit 30 detects that the guide pin 20 is inserted into the arm-holding unit 19 and the arm 16 is held by the arm-holding unit 19.

When the arm 16 (guide pin 20) is not held by the arm-holding unit 19, the light which is irradiated from the illumination unit is detected by the illumination detecting unit. At this time, the arm-holding unit 30 detects that the guide pin 20 is not inserted into the arm-holding unit 19 and the arm 16 is not held by the arm-holding unit 19.

While the guide pin 20 inserted into the arm-holding unit 19 is detected by the illumination unit and the light sensor of the illumination detecting unit, the arm-holding detection unit 30 can also detect whether or not the rod portion to be inserted into the through-hole at the end of the guide pin 20 is inserted by the above-described fixation mechanism so as to detect the holding condition of the arm-holding unit 19.

Also, the reading device 34 converts the latent images accumulated in the imaging plate as image data and outputs the converted data. The imaging plate has fluorescent material, and accumulates in the fluorescent material the 2-dimensional X-ray energy pattern which is generated from the X-ray generation unit 14 and penetrated through the object, as latent images. The reading device 34 is provided with devices such as a laser scanning means, a photoelectron multiplier and an A/D converter. The laser scanning means scans laser beams in the latent images accumulated as electrons in the fluorescent material of the imaging plate to read out an image. The fluorescent material in which laser beams are scanned emits light in accordance with the irradiated X-ray amount, and the latent images are converted into light photons. The light photon is converted into analogue electric signals by the photoelectron multiplier, then converted into digital signals by the A/D converter, and obtained as image data.

The PC (image storage/processing unit) 35 executes predetermined image processing with respect to the image data output from the reading device 34. The predetermined image processing is, for example a dynamic range compression process or a frequency enhancement process.

Also, an operation unit 37 is formed in such a manner that a touch panel or a keyboard is mounted on the upper surface of the carriage 11 for operating devices such as the power control unit 31.

The power control unit 31 controls the electric power to be provided from the battery 38 by distinguishing the components of the movement-related sections 40 that are relevant to the movement of the mobile X-ray device and the components of non-movement-related sections 54 other than the movement-related sections 40 and are irrelevant to the movement of the mobile X-ray device.

Figure 4:
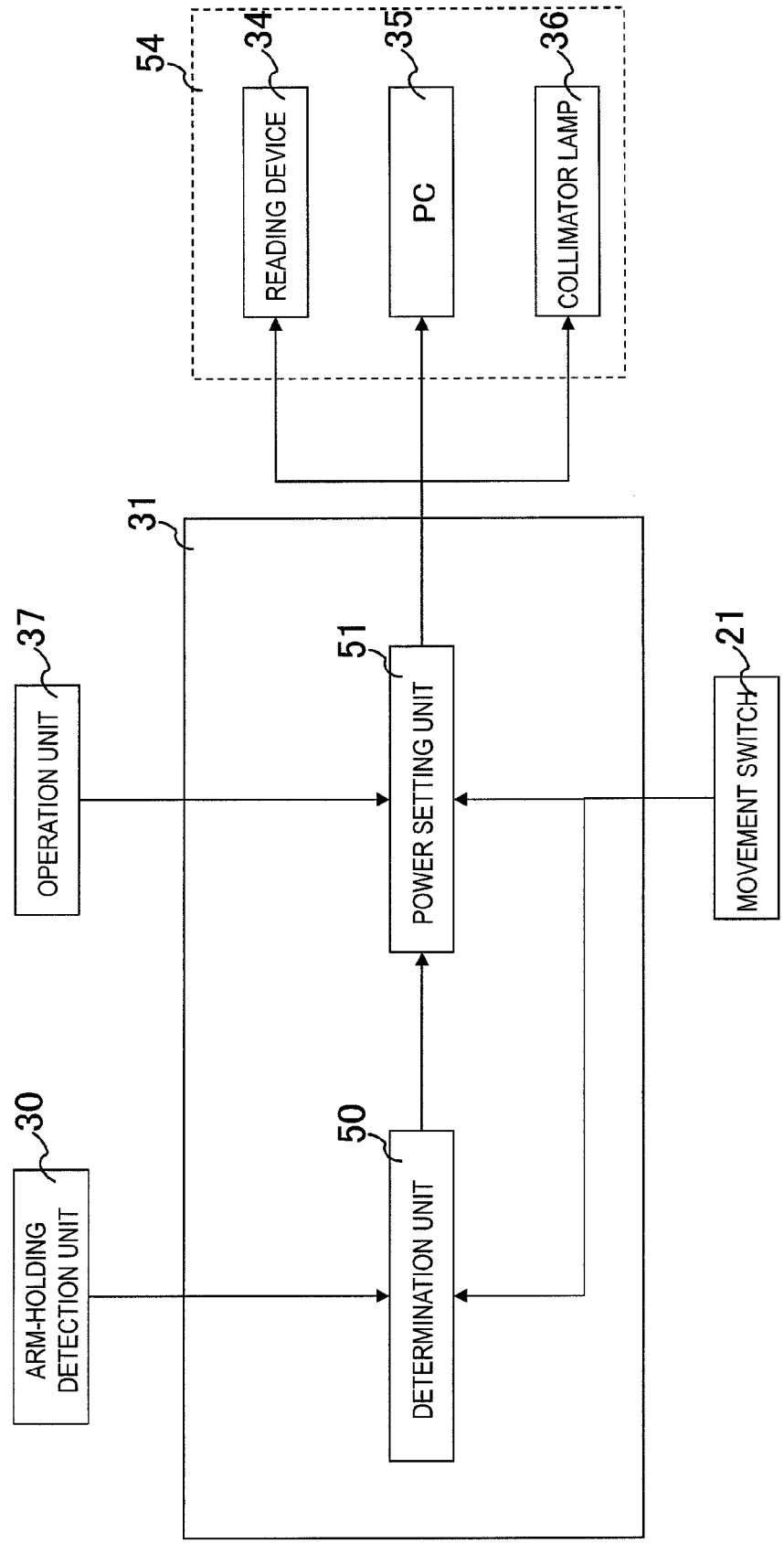
FIG. 4 is a view showing a power control unit 31 of the mobile X-ray device related to the present invention.

Here, the power control unit 31 will be described in detail referring to FIG. 4. The power control unit 31 is provided with a determination unit 50 configured to determine the movement condition of the mobile X-ray device, and a power setting unit 51 configured to set the electric power to be supplied to the components of the non-movement-related sections other than the movement-related sections 40 and are irrelevant to the movement of the mobile X-ray device, on the basis of the movement condition determined by the determination unit 50. The components of the movement-related section 40 that are relevant to the movement of the mobile X-ray device are, for example the movement switch 21, the power control unit 31, the wheel driving unit 32 and the wheel locking unit 33. The components of the non-movement-related sections 54 that are irrelevant to the movement of the mobile X-ray device are, for example the reading unit 34, the PC 35 and the collimator lamp 36.

The determination unit 50, when the arm-holding detection unit 30 detected that the guide pin 20 is not inserted into the arm-holding unit 19, i.e. that the arm 16 is not held by the arm-holding unit 19, determines that the mobile X-ray device is in an imaging mode as shown in FIG. 1.

Also, the determination unit 50, when the arm-holding detection unit 30 detected that the guide pin 20 is inserted into the arm-holding unit 19, i.e. that the arm 16 is held in the arm-holding unit 19, determines that the mobile X-ray device is in a moving mode as shown in FIG. 2. The determination unit 50 outputs the information on the determined movement condition (imaging mode or moving mode) to the power setting unit 51.

When the determination unit 50 determines that the mobile X-ray device is in a moving mode, the power setting unit 51 reflects the power condition which is set in advance by the operation unit 37, and sets the power-off mode to turn off the electric power to be supplied to the components of the non-movement-related sections 54 that are irrelevant to the movement of the mobile X-ray device or the power-saving mode to reduce the electric power to be supplied to the components of the non-movement-related sections 54. The operation unit is capable of selecting the power-off mode or the power-saving mode for the electric power to be supplied to the components of the non-movement-related sections 54 and reflecting the selected information to the power setting unit 51.

In particular, the mobile X-ray device in the present embodiment comprises the main body 10, the carriage 11 on which the main body 10 is mounted, the X-ray generation unit 14 provided with an X-ray tube for generating an X-ray, the X-ray collimator 15 configured to adjust the irradiation range of the X-ray, the arm 16 configured to support the X-ray generation unit 14, the columnar support 17 which is disposed on the carriage to support the arm 16 and the battery 38 for providing electric power to the respective components, and is characterized in further comprising the determination unit 50 configured to determine the movement condition of the mobile X-ray device (carriage 11) and the power setting unit 51 configured to set the electric power to be supplied from the battery 38 to the components 34, 35 and 36 of the non-movement-related sections that are irrelevant to the movement of the mobile X-ray device on the basis of the movement condition which is determined by the determination unit 50.

(Power-Off Mode)

First, the power-off mode for turning off the electric power to be supplied to the components of the non-movement-related sections 54 that are irrelevant to the movement of the mobile X-ray device will be described.

The power-off mode is selected by the operation unit 37 in advance. The operation unit 37 is provided with the power-off mode button for starting the power-off mode and the power-off mode releasing button for ending the power-off mode. The operator can select the power-off mode by pushing the power-off mode button of the operation unit 37. The power setting unit 51 may also select the power-off mode automatically on the basis of the previously set X-ray imaging schedule.

When the determination unit 50 determines that the mobile X-ray device is in the moving mode, the power setting unit 51 turns off the electric power to be supplied to the reading device 34, the PC 35 and the collimator lamp 36 in the non-movement-related sections 54 that are irrelevant to the movement of the mobile X-ray device. That is, the electric power is not supplied from the battery 38 to the components of the non-movement-related sections 54.

When the mobile X-ray is in a moving mode, the movement switch 21 need to be triggered under control of the power control unit 31 to release the brake of the wheels 12 put on by the wheel locking unit 33 so that the wheels 12 can be rotated by the wheel driving unit 32. Given this factor, the power setting unit 51, when the mobile X-ray device is in the moving mode, supplies the electric power from the battery 38 to the movement-related sections 40 including the moving switch 21, the power control unit 31, the wheel driving unit 32 and the wheel locking unit 33.

Accordingly, when the mobile X-ray device is in the moving mode, the electric power to be supplied from the battery will be supplied not to the components of the non-movement-related sections 54 but only to the components of the movement-related sections 40, thus the power consumption of the battery 38 can be effectively minimized which enables the battery to last longer.

When the movement of the mobile X-ray device in the moving mode is completed, the operator pulls out the guide pin 20 from the arm-holding unit 19 and moves to the imaging mode of the mobile X-ray device shown in FIG. 1. At this time, the arm-holding detection unit 30 detects that the guide pin 20 is not inserted into the arm-holding unit 19. The determination unit 50 then determines that the arm 16 is not held by the arm-holding unit 19, thus the state of the device as the imaging mode.

When the determination unit 50 determines that the mobile X-ray device is in the imaging mode, the power setting unit 51 cancels the power-off mode which turned off the electric power to be supplied to the components of the non-movement-related sections 54 that are irrelevant to the movement of the mobile X-ray device. Accordingly, the electric power is now supplied from the battery 38 to the reading device 34, the PC 35 and the collimator lamp 36 which are the components of the non-movement-related sections 54.

While the power-off mode is canceled when the mobile X-ray device is determined being in the imaging mode in the above description, the operator can also cancel the power-off mode by pushing the power-off mode cancel button of in the operation unit 37.

Also, when the determination unit 50 determines that the mobile X-ray device is in the imaging mode, since the mobile X-ray device is not being moved, the power setting unit 51 can turn off the electric power being supplied from the battery 38 to the movement switch 21, the wheel driving unit 32 and the wheel locking unit 33 of the movement-related sections 40 that are relevant to the movement of the mobile X-ray device. Although the power control unit 31 is included in the movement-related sections 40, electric power is to be constantly supplied thereto due to the need for controlling the respective components.

There are occasions in the imaging mode that the carriage 11 is slightly moved at bedside for setting the imaging range of an object. At this time, the operator can also trigger a micromotion switch (not shown) disposed on the X-ray collimator 15 to cause the power setting unit 51 temporarily supply the electric power from the battery 38 to the components of the movement-related sections 40 that are relevant to the movement of the mobile X-ray device.

Also, while the power setting unit 51, when the mobile X-ray device is in the moving mode, turns off the electric power to be supplied to the reading device 34 of the non-movement-related sections 54 that are irrelevant to the movement of the mobile X-ray device in the above-description, the power setting unit 51 can also set the electric power to be temporarily supplied only to the reading device 34 of the non-movement-related sections 54. Accordingly, even when the mobile X-ray device is in the moving mode, the operator can use the reading device 34 and display the image data accumulated in the imaging plate via the PC 35 on a display unit (not shown) which is on the operation unit 37.

(Power-Saving Mode)

Next, the power saving mode for saving the electric power to be supplied to the components of the non-movement-related sections 54 that are irrelevant to the movement of the mobile X-ray device will be described.

The power-saving mode is selected via the operation unit 37 in advance. The operation unit 37 is provided with the power-saving mode button for starting the power-saving mode and the power-saving mode cancel button for ending the power-saving mode. The operator can select the power-saving mode by pushing the power-saving mode button on the operation unit 37. The power setting unit 51 may also select the power-saving mode automatically on the basis of the previously set X-ray imaging schedule.

When the determination unit 50 determines that the mobile X-ray device is in the moving mode, the power setting mode minimizes the electric power provided from the battery 38 to the reading device 34, the PC 35 and the collimator lamp 36 in the non-movement-related sections 54 that are irrelevant to the movement of the mobile X-ray device.

The power-saving mode is the mode to save power consumption. For example, in the power-saving mode of the reading device 34, the power setting unit 51 sets the electric power not to be supplied to one of the components of the laser scanning means, the photoelectron multiplier and the A/D converter. In concrete terms, the power setting unit 51 sets the electric power to be constantly supplied from the battery 38 to the components of the reading device 34 that start up slowly (for example, the photoelectron multiplier), and the electric power from the battery 38 to the components of the reading device 34 that start up quickly (for example, the laser scanning means and the A/D converter) to be turned off.

Also, in the power-saving mode of the PC 35, the power setting unit 51 constrains the unnecessary electric power to be supplied from the battery 38 to the components of the PC 35 while maintaining the operating condition of the PC 35, or writes in the last-minute operative state of the PC 35 in hard disk without maintaining the operative condition of the PC 35 and stops the rotation of the hard disk.

Also, in the power-saving mode of the collimator lamp 36, the power setting unit 51 constrains the electric power to be supplied from the battery 38 to the collimator lamp 36.

In other words, the electric power to be supplied from the battery 38 to the components of the non-movement-related sections 54 is minimized, thereby facilitating the battery 38 to last longer. Meanwhile, the electric power from the battery 38 to the components of the movement-related sections 40 is supplied constantly.

Then when the determination unit 50 determines that the mobile X-ray device is in the imaging mode, the power setting unit 51 cancels the power-saving mode which has been minimizing the electric power to be supplied to the components of the non-movement-related sections 54 that are irrelevant to the movement of the mobile X-ray device. Accordingly, the electric power from the battery 38 to the reading device 34, the PC 35 and the collimator lamp 36 of the non-movement-related sections 54 is supplied without being minimized.

While the power-saving mode is cancelled when the mobile X-ray device is determined being in the imaging mode in the above-description, the operator may also push the power-saving mode cancel button to cancel the power-saving mode.

Next, the operation in the first embodiment will be described referring to FIG. 5.

(S1)

As shown in FIG. 1, in the imaging mode of the mobile X-ray device for executing X-ray imaging, the irradiation field of an X-ray is adjusted by the X-ray collimator 15 and the X-ray is generated with respect to an object by the X-ray generation unit 14 for executing the X-ray imaging. The 2-dimensional X-ray energy pattern which is penetrated through an object is accumulated as latent images in the fluorescent material of the imaging plate which is disposed facing the X-ray generation unit 14.

(S2)

The operator selects the power-off mode or the power-saving mode by pressing the power-off mode button for starting the power-off mode to turn off the electric power to be supplied to the components of the non-movement-related sections 54 that are irrelevant to the movement of the mobile X-ray device or the power-saving mode button for starting the power-saving mode to reduce the electric power to be supplied to the components of the non-movement-related sections 54.

(S3)

When the arm-holding detection unit 30 detects that the guide pin 20 is inserted into the arm-holding unit 19 and the arm 16 is held by the arm-holding unit 19, the determination unit 50 determines that the mobile X-ray device is in the moving mode as shown in FIG. 2.

(S4)

The power setting unit 51, on the basis of the information on the power-off mode or the power-saving mode selected via the operation unit 37, sets the power-off mode or the power-saving mode to the components of the non-movement-related sections 54 that are irrelevant to the movement of the mobile X-ray device. Accordingly, the power setting unit 51 can turn off or minimize the electric power to be supplied to the reading device 34, the PC 35 and the collimator lamp 36 of the non-movement-related sections 54.

(S5)

When the transfer of the mobile X-ray device is completed, the operator selects whether or not to execute X-ray imaging again using the operation unit 37. In the case that the X-ray imaging is to be performed again, S6 is carried out. In the case that the X-ray imaging is not to be performed again, the operation is ceased.

(S6)

The arm-holding detection unit 30 detects that the guide pin 20 is not inserted into the arm-holding unit 19 and the arm 16 is not held by the arm-holding unit 19, and the determination unit 50 determines that the device is in the imaging mode.

(S7)

The power setting unit 51 cancels the power-off mode or the power-saving mode for turning off or minimizing the electric power to be supplied to the components of the non-movement-related sections 54 that are irrelevant to the movement of the mobile X-ray device.

After S7 is carried out, the process is returned to S1 and the same operation from S1 to S7 will be repeated.

As described above, the present embodiment can detect the movement condition of the mobile X-ray device from the state of the respective components, and control the power supply to the components of the non-movement-related sections that are irrelevant to the movement of the mobile X-ray device. The present embodiment can also effectively reduce the power consumption of the battery 38, which enables the battery 38 to last longer.

While the above-described present embodiment includes the reading device 34, the PC 35 and the collimator lamp 36 as the components of the non-movement-related sections 54 that are irrelevant to the movement of the mobile X-ray device, other components (X-ray generation unit 14, etc.) may also be included therein.

Also while the latent images of X-rays are accumulated in the imaging plate and the accumulated latent images are converted by the reading device 34 into image data in the above embodiment, the imaging plate and the reading device 34 can also be replaced with a flat panel detector (FPD). The flat panel detector (FPD) is a planar detector provided with a two-dimensionally arrayed transistor and a transducing membrane that transduce the X-ray into electric signals. In this case, the flat panel detector (FPD) is connected to the PC (image storage/processing unit) 35, and the PC (image storage/processing unit) 35 executes predetermined image processing with respect to the image data output from the flat panel detector (FPD).

Embodiment 2

Figure 6:
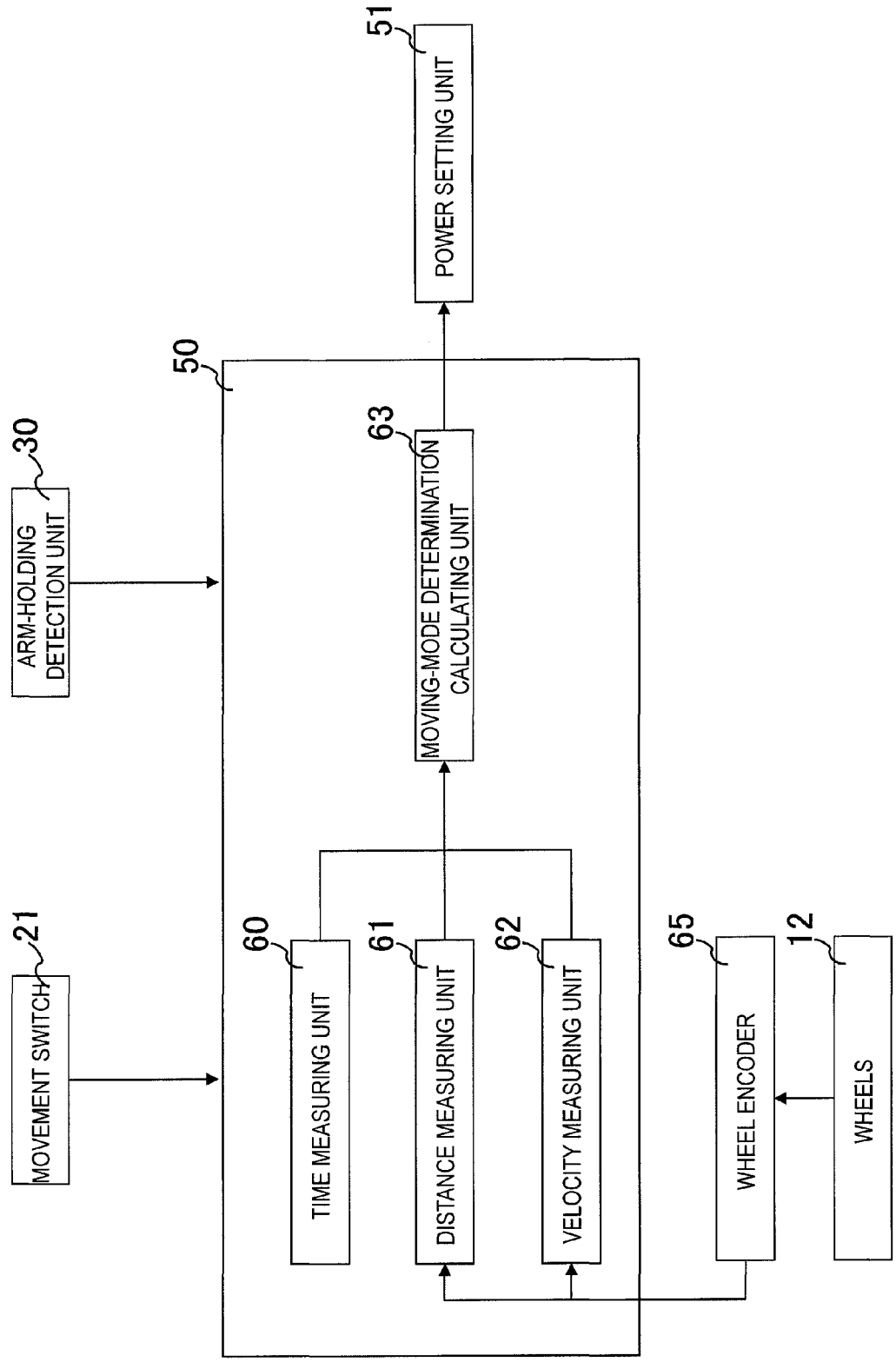
FIG. 6 is a view showing a second embodiment of the mobile X-ray device related to the present invention.

Next, the second embodiment will be described referring mainly to FIG. 6. The difference from the first embodiment is that the determination unit 50 determines the movement condition of the mobile X-ray device based on any information on the moving time, moving distance, moving velocity, etc. of the mobile X-ray device (carriage 11).

The determination unit 50 is provided with one of a time measuring unit 60 configured to measure the moving time of a mobile X-ray device, a distance measuring unit 61 configured to measure the moving distance of a mobile X-ray device or a velocity measuring unit 62 configured to measure the moving velocity of the mobile X-ray device, and a moving-mode determination calculating unit 63 configured to determine whether the mobile X-ray device is in the moving mode on the basis of the movement information of the mobile X-ray device.

The moving-mode determination calculating unit 63 determines that the mobile X-ray device is in the moving mode on the basis of the time information measured by the time measuring unit 60. The time measuring unit 60 measures the length of time that the movement switch 21 on the operation handle 18 is being pressed by the operator. In concrete terms, when the movement switch is pressed, the information on pressing is transmitted from the movement switch 21 to the time measuring unit 60, and the time measuring unit 60 starts the measurement of the time spent on the pressing of the switch. The time information which is measured by the time measuring unit 60 is output to the moving-mode determination calculating unit 63.

When the movement switch 21 of the operation handle 18 is being pressed, for example for more than 5 seconds, it is likely that the mobile X-ray device is being transferred to another patient's room. Given this factor, if the length of time which is measured by the time measuring unit 60 surpasses a preset threshold time (for example, more than 5 seconds), the moving-mode determination calculating unit 63 determines that the mobile X-ray device is in the moving mode. If the length of time which is measured by the time measuring unit 60 is less than a preset threshold time (for example, less than 5 seconds), the moving-mode determination calculating unit 63 determines that the mobile X-ray device is not in the moving mode.

Also, the moving-mode determination calculating unit 63 determines that the mobile X-ray device is in the moving mode on the basis of the distance information measured by the distance measuring unit 61. The distance measuring unit 61 measures the moving velocity of the carriage 11 in the mobile X-ray device on the basis of a wheel encoder 65 which is disposed in the wheels 12 of the carriage 11. The wheel encoder 65 has plural magnets and the elements that detect the position of the magnets, and generates a pulse each time that the wheel 12 rotates by a predetermined angle (for example, 30 degrees). In concrete terms, when the movement switch 21 is pressed, the pressing information is transmitted from the movement switch 21 to the time measuring unit 60, and the distance measuring unit 61 starts the distance measurement of the carriage 11 using the wheel encoder 65.

When the movement switch 21 of the operation handle 18 is pressed by the operator and the moving distance of the carriage 11 measured by the wheel encoder 65 and the distance measuring unit 61 is, for example more than 3 m, it is likely that the mobile X-ray device is being transferred to another patient's room. Given this factor, if the distance which is measured by the distance measuring unit 61 surpasses a preset threshold value (for example, more than 3 m), the moving-mode determination calculating unit 63 determines that the mobile X-ray device is in the moving mode. If the distance measured by the distance measuring unit 61 is less than a preset threshold value (for example, less than 3 m), the moving-mode determination calculating unit 63 determines that the mobile X-ray device is not in the moving mode.

Also, the moving-mode determination calculating unit 63 determines that the mobile X-ray device is in the moving mode on the basis of the velocity information measured by the velocity measuring unit 62. The velocity measuring unit 62 measures the moving velocity of the carriage 11 in the mobile X-ray device based on the wheel encoder 65 which is disposed in the wheel 12 of the carriage 11. In concrete terms, when the movement switch 21 is pressed, the pressing information is transmitted from the movement switch 21 to the time measuring unit 60, and the velocity measuring unit 62 starts the velocity measurement of the carriage 11 using the wheel encoder 65.

When the movement switch 21 of the operation handle 18 is pressed by the operator and the moving velocity of the carriage measured by the wheel encoder 65 and the velocity measuring unit 62 is, for example more than 5 (km/h), it is likely that the mobile X-ray device is being transferred to another patient's room. Given this factor, if the velocity measured by the velocity measuring unit 62 is more than a preset threshold value (for example, more than 5 (km/h)), the moving-mode determination calculating unit 63 determines that mobile X-ray device is in the moving mode. If the velocity measured by the velocity measuring unit 62 is less than a preset threshold value (for example, less than 5 (km/h)), the moving-mode determination calculating unit 63 determines that the mobile X-ray device is not in the moving mode.

Then when the mobile X-ray device is determined as being in the moving mode by the moving-mode determination calculating unit 63 (determination unit 50) and one of the time measuring unit 60, the distance measuring unit 61 and the velocity measuring unit 62, the power setting unit 51 reflects the power condition which is previously set by the operation unit 37 and sets the power-off mode that turns off the electric power to be supplied to the components of the non-movement-related sections 54 that are irrelevant to the movement of the mobile X-ray device or the power-saving mode that reduces the electric power to be supplied to the non-movement-related sections 54.

Figure 5:
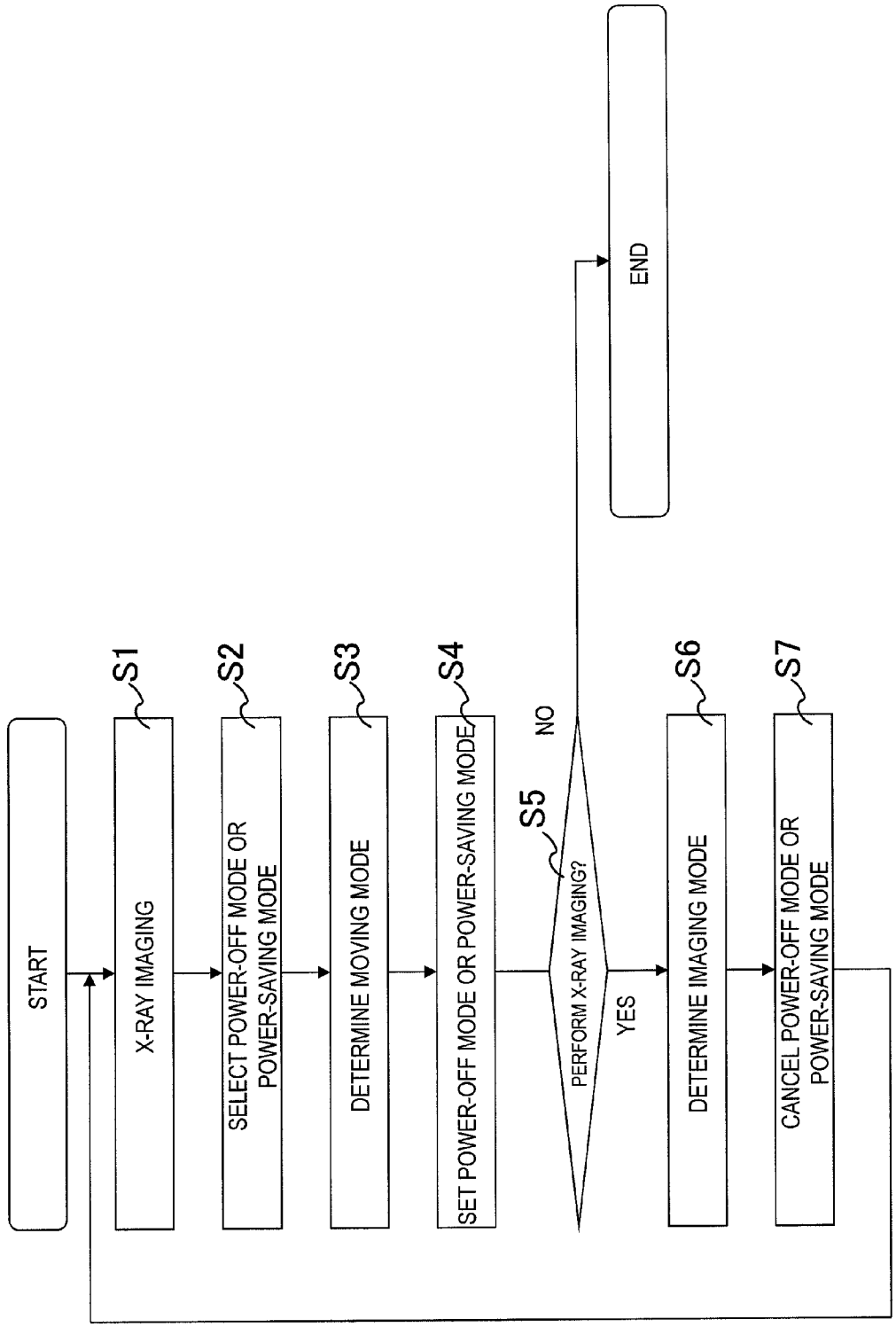
FIG. 5 is a flowchart showing the operation of the mobile X-ray device related to the present invention.

The operation in the present embodiment will be omitted here since the process of S1, S2, S4~S7 in the operation indicated in FIG. 5 are the same, and the operation can be carried out by replacing the process of S3 with the above-description regarding the determining 50.

Also, the moving-mode determination calculating unit 63 may also combine the time information measured by the time measuring unit 60, the distance information measured by the distance measuring unit 61 and the velocity information measured by the velocity measuring unit 62 for determining that the mobile X-ray device is in the moving mode. For example, when the time which is measured by the time measuring unit 60 is more than a preset threshold time (for example, more than 5 seconds) and the velocity which is measured by the velocity measuring unit 62 is more than a preset threshold value (for example, more than 5 (km/h)), the moving-mode determination calculating unit 63 determines that the mobile X-ray device is in the moving mode.

As described above, in accordance with the present embodiment, it is possible to detect the movement condition of a mobile X-ray device from any information of the moving time, moving distance or moving velocity, so as to control the power supply to the components of the non-movement-related sections that are irrelevant to the movement of the mobile X-ray device.

Embodiment 3

Next, the third embodiment will be described referring to FIG. 7. The difference from the first and second embodiments is that an operator respectively selects the power-off mode or the power-saving mode to be allotted to each component of the non-movement-related sections 54 that are irrelevant to the movement of the mobile X-ray device and sets the power condition.

FIG. 7 is a view showing a pattern of the operation unit 37. The operation unit 37 is provided with the power-off mode button 70 for starting the power-off mode, the power-off mode cancel button 71 for ending the power-off mode, the power-saving mode button 72 for starting the power-saving mode and the power-saving mode cancel button 73 for ending the power-saving mode. The operation unit 37 in the present embodiment is a touch panel, and various setting can be executed by pushing the respective buttons on the top surface of the operation unit 37.

Selection of the power-off mode or the power-saving mode of the reading device 34 will be described. First, the operator presses the periphery of the reading device which is displayed on the operation unit 37 to select the reading device. When the reading device is selected, a selection mark 75 is displayed as indicated in FIG. 7. Then the operator presses the power-off mode button 70 for starting the power-off mode or the power-saving button 72 for starting the power-saving mode. It is assumed in the present embodiment that the power-saving button 72 is pressed. As shown in FIG. 7, the power-saving mode corresponding to the reading device is displayed as "ON". Accordingly, the power-saving mode is selected via the operation unit 37 with respect to the reading device 34 which is one of the components of the non-movement-related sections 54.

In the same manner as the pattern of the reading device 34, the power-off mode or the power-saving mode for the PC 35 and the collimator lamp 36 can also be selected via the operation unit 37. In the present embodiment, the power-saving mode is selected for the PC 35 and the power-off mode is selected for the collimator lamp 36 via the operation unit 37.

As described above, in accordance with the present embodiment, it is possible to respectively select the power-off mode or the power-saving mode to be allotted to each component of the non-movement-related sections 54 that are irrelevant to the movement of the mobile X-ray device via the operation unit 37. In other words, the operator can control the power supply from the battery 38 according to the characteristic of the respective components.

Embodiment 4

Next, the fourth embodiment will be described referring to FIG. 8. The difference from the first~third embodiments is that the power-off mode or the power-saving to be allotted to each component in the non-movement-related sections 54 that are irrelevant to the movement of the mobile X-ray device is respectively set as the initial setting.

For the reading device 34, the PC 35 and the collimator lamp 36 which are the components of the non-movement-related sections 54 that are irrelevant to the movement of the mobile X-ray device, the power-off mode or the power-saving mode is selected in advance via the operation unit 37. Then the selected power-off mode or power-saving mode is stored in a storage unit in the power setting unit 31 which is not shown in the diagram as the initial setting. Even when the power-off mode or the power-saving mode is not selected by the operation unit 37, the non-selected information indicating that neither the power-off mode nor the power-saving mode is selected is stored in the storage unit.

Each time that the mobile X-ray device is used, the power-off mode, the power-saving mode or non-selected information corresponding to the reading device 34, the PC 35 and the collimator lamp 36 is read out from the storage unit, and the read out information is selected and displayed, for example as shown in FIG. 8. In the present embodiment, the power-saving mode is selected for the reading device 34, the power-off mode is selected for the collimator lamp 36, and neither of these modes is selected for the PC 35.

When the power-off mode, the power-saving mode and non-selected information to be allotted to each component in the non-movement-related sections 54 are respectively set as the initial setting, a default mark 80 is displayed on the operation unit 37. When the operator changes the setting of the power-off mode or the power-saving mode, etc. via the operation unit 37, the default mark 80 displayed on the operation unit 37 is deleted.

In accordance with the present embodiment, it is possible to respectively select the power-off mode or the power-saving mode to be allotted to each component (the reading device 34, the PC 35 and the collimator lamp 36) of the non-movement-related sections 54 that are irrelevant to the movement of the mobile X-ray device as the initial setting. In other words, it is not necessary for the operator to perform power control of the battery 38 for each use of the mobile X-ray device as described in the third embodiment.

Embodiment 5

Next, the fifth embodiment will be described referring to FIG. 9. The difference from the first~fourth embodiments is that the power setting unit 51 sets the power-off mode or the power-saving mode on the basis of the information on whether to perform X-ray imaging again.

(S10)

As shown in FIG. 9, in the imaging mode of the mobile X-ray device for executing X-ray imaging, the X-ray imaging is performed by adjusting the irradiation field of an X-ray by the X-ray collimator 15 and generating an X-ray with respect to an object by the X-ray generation unit 14.

(S11)

When the X-ray imaging is completed, the operator selects whether to execute X-ray imaging again using the operation unit 37. In the case that the X-ray imaging is to be performed again, the setting of power-saving mode in S12 is to be carried out. If the X-ray imaging is not to be performed again, the setting of power-off mode in S15 is to be carried out.

(S12)

When the selection is made to perform the X-ray imaging again via the operation unit 37, the power setting unit 51 sets the power-saving mode to reduce the electric power to be supplied to the components of the non-movement-related sections 54 that are irrelevant to the movement of the mobile X-ray device.

(S15)

When the selection is made not to perform the X-ray imaging again via the operation unit 37, the power setting unit 51 sets the power-off mode to turn off the electric power to be supplied to the components of the non-movement-related sections 54 that are irrelevant to the mobile X-ray device. Then the mobile X-ray device is transferred to a waiting position (a store room, etc.), and the operation is ended.

(S13)

The arm-holding detection unit 30 detects that the guide pin 20 is not inserted into the arm-holding unit 19 and the arm 16 is not held by the arm-holding unit 19, the determination unit 50 determines that the device is in the imaging mode.

(S14)

The power setting unit 51 cancels the power-saving unit which has been minimizing the electric power to be supplied to the components of the non-movement-related sections 54 that are irrelevant to the movement of the mobile X-ray device.

After S14 is executed, the process is returned to S10 and the same operation of the S10~S15 is carried out.

Since the content of the power-off mode and the power-saving mode is described in the first embodiment, the description of the power-off mode and the power-saving mode will be omitted in the present embodiment.

While the first~fifth embodiments have been described above, the mobile X-ray device of the present invention can be used by suitably combining the first~fifth embodiments. For example, the determination unit 50 can determine the movement condition of the mobile X-ray device by combining the information on the arm-holding condition detected by the arm-holding detection unit 30 which is described in the first embodiment and the information on the movement condition of the mobile X-ray device (carriage 11) which is described in the second embodiment. In concrete terms, when the arm-holding detection unit 30 detects that the guide pin 20 is inserted into the arm-holding unit 19 and the arm 16 is held by the arm-holding unit 19, as well as the moving-mode determination calculating unit 63 determined that the mobile X-ray device is in the movement condition based on the movement information detected by any of the time measuring unit 60, the distance measuring unit 61 and the velocity measuring unit 62, the determination unit 50 determines that the mobile X-ray device is in the moving mode.

DESCRIPTION OF REFERENCE NUMERALS

10 main body
11 carriage
12 wheel
13 wheel
14 X-ray generation unit
15 X-ray collimator
16 arm
17 columnar support
18 operation handle
19 arm-holding unit
20 guide pin
30 arm-holding detection unit
31 power control unit
32 wheel driving unit
33 wheel locking unit
34 reading device
35 PC
36 collimator lamp
37 operation unit
38 battery

The invention claimed is:

1. A mobile X-ray device comprising:
a main body;
a carriage on which the main body is mounted;
an X-ray generation unit provided with an X-ray tube for generating an X-ray;
an X-ray collimator configured to adjust an irradiation field of the X-ray;
an arm configured to support the X-ray generation unit;
a columnar support which is disposed on the carriage to support the arm;
a battery configured to supply electric power to respective components;
a determination unit configured to determine a movement condition of the mobile X-ray device;
a power setting unit configured to set the electric power to be supplied from the battery to components of non-movement-related sections that are irrelevant to a movement of the mobile X-ray device, based on the movement condition determined by the determination unit,
wherein the power setting unit, in response to the determination unit determining that the mobile X-ray device is in a moving mode:
sets a power-off mode which turns off the electric power to be supplied from the battery to the components of the non-movement-related sections, or
sets a power-saving mode to reduce the electric power to be supplied from the battery to the components of the non-movement-related sections,
wherein the power setting unit sets the power-off mode in response to a selection being made not to perform an X-ray imaging again, and
wherein the power setting unit sets the power-saving mode in response to a selection being made to perform the X-ray imaging again; and
an operation unit configured to:
end the power-off mode, which was set by the power setting unit, or
end the power-saving mode, which was set by the power setting unit.

2. The mobile X-ray device according to claim 1, wherein the power setting unit, in response to the determination unit determining that the mobile X-ray device is in an imaging mode, sets the power-off mode to turn off the electric power to be supplied from the battery to components of movement-related sections that are relevant to the movement of the mobile X-ray device.

3. The mobile X-ray device according to claim 1, wherein the components of the non-movement-related sections are the components other than movement-related sections that are relevant to the movement of the mobile X-ray device.

4. The mobile X-ray device according to claim 1,
wherein in response to the determination unit determining that the mobile X-ray device is in the moving mode, the power setting unit is configured to set one of:
the power-off mode to turn off the electric power to be supplied from the battery to the components of the non-movement-related sections, and
the power-saving mode to reduce the electric power, and
wherein the operation unit is configured to select the power-off mode or the power-setting mode for the electric power to be supplied to the components of the non-movement-related sections.

5. The mobile X-ray device according to claim 1, wherein the component of the non-movement-related sections comprises at least one of:
a reading device configured to convert the latent images accumulated in an imaging plate into image data and output the converted data,
a PC configured to perform predetermined imaging process with respect to the image data output from the reading device, and
an collimator lamp which is provided in the X-ray collimator to light the irradiation range of an X-ray.

6. The mobile X-ray device according to claim 1, comprising:
an arm-holding unit configured to hold the arm while the mobile X-ray device is being transferred; and
an arm-holding detection unit configured to detect an arm-holding condition of the arm, wherein the determination unit is further configured to determines the movement condition of the mobile X-ray device on a basis of the detected arm-holding condition.

7. The mobile X-ray device according to claim 1, wherein the determination unit is further configured to determines the movement condition based on information of a moving time, moving distance and moving velocity of the mobile X-ray device.

8. The mobile X-ray device according to claim 2, further comprising a storage unit configured to store a setting of the power-off mode or the power-saving mode which is selected in advance via the operation unit as an initial setting.

9. A control method of a mobile X-ray device, comprising:
   determining a movement condition of the mobile X-ray device;
   setting the electric power to be supplied from a battery to components of non-movement-related sections that are irrelevant to a movement of the mobile X-ray device on a basis of the movement condition,
   wherein in response to the movement condition of the mobile X-ray device is determined to be in a moving mode:
      setting a power-off mode which turns off the electric power to be supplied from the battery to the components of the non-movement-related sections, or
      setting a power-saving mode to reduce the electric power to be supplied from the battery to the components of the non-movement-related sections, and
   wherein the setting the power-off mode or the setting the power-saving mode are based on selected information on whether to perform an X-ray imaging; and
at least one of:
   ending the power-off mode set by the power setting unit, or
   ending the power-saving mode set by the power setting unit.

* * * * *